United States Patent [19]

Brown

[11] Patent Number: 4,659,673

[45] Date of Patent: Apr. 21, 1987

[54] REPLICATOR FOR CULTURES OF MICROORGANISMS

[76] Inventor: Lewis R. Brown, 5 Hialeah Dr., Starkville, Miss. 39759

[21] Appl. No.: 793,959

[22] Filed: Nov. 1, 1985

[51] Int. Cl.[4] .............................................. C12M 1/32
[52] U.S. Cl. .................................... 435/293; 435/300
[58] Field of Search ............... 435/287, 285, 292, 293, 435/297, 298, 300, 301

[56] References Cited

U.S. PATENT DOCUMENTS 2,533,089 12/1950 Brewer .......................... 435/298 X
2,956,931 10/1980 Goldberg ............................ 435/293

FOREIGN PATENT DOCUMENTS 2927141 7/1979 Fed. Rep. of Germany ...... 435/293

OTHER PUBLICATIONS

"The Repliplate (TM) Colony Transfer Pad: A New Device for Replicating Microbial Colonies", Bio Techniques, Mar./Apr. 1985, pp. 152-154.
"Instructions for Use of Repliplate (TM) Colony Transfer Pads", FMC Bioproducts, 5 Maple Street, Rockland, ME 04841, 1985.
"Introducing Repliplate", FMC Bioproducts, (undated).

Primary Examiner—Alan Cohan
Attorney, Agent, or Firm—Ferris M. Stout

[57] ABSTRACT

An improved device for replicating cultures of microorganisms grown in petri plates which pierces colonies with an array of fine needles. The device is capable of at least ten replications, and will replicate virtually any colony.

1 Claim, 3 Drawing Figures

REPLICATOR FOR CULTURES OF MICROORGANISMS

BACKGROUND OF THE INVENTION

1. Field of the Invention

This invention is in the field of sampling and culturing microorganisms; more specifically, in the field of replicating cultures of microorganisms.

2. The Prior Art

A microbiologist often needs to replicate a mixed culture of microorganisms which are growing in a petri plate. He/she needs to transfer an inoculum of each and every colony growing on the surface of one plate to the agar surface of a new plate or plates.

A conventional method for accomplishing the transfer uses a round block of wood (or other material) which fits into the petri plate in which the master culture is growing. The bottom of the block is covered with velvet. The (sterilized) velvet-covered surface of the block is gently but firmly pressed against the surface of the master culture; then it is pressed against the agar surface of one or more freshly prepared petri plates. If the procedure is successful, the newly inoculated plates will grow colonies which are exact replicas of the colonies growing in the master culture.

The velvet-covered block procedure has certain drawbacks. Some colonies in the master culture may be raised colonies. Pressing the block against the raised colonies is likely to mash them and spread them out on the velvet, possibly inhibiting the growth on the new plate of neighboring colonies. On the other hand, flat colonies are likely to be bridged over by the velvet, and thereby be absent when the new plate is cultured. Actinomycete colonies, which are quite hard, are often not picked up on the velvet. Finally cleaning and sterilizing the velvet surface after each use quickly destroys the velvet.

A new device (patent pending) for replicating master cultures is being sold under the trade name Repli-Plate TM by FMC Marine Colloids BiProducts Co. The device, which is disposable, comprises a synthetic sponge fixed into the lid of a conventional petri plate. According to promotional literature on the device ("The RepliPlate TM Colony Pad: A New Device for Replicating Microbial Colonies", by Foner P. Curtis and Donald W. Renn) will replicate a plate containing *Escherichia coli* six times, a yeast, *Saccharomyces cerevisiae*, four times, and *Bacillus subtilis* colonies only twice. Although it is disposable, the RepliPlate TM suffers from the first three of the disadvantages referred to above for the velvet-covered block.

A need therefore exists for a disposable device which will reliably and repetitively replicate mixed cultures of microorganisms of varying colonial characteristics. Alternatively there is need of such a device which is readily and repeatedly reuseable.

SUMMARY OF THE INVENTION (In what follows, we refer, for clarity's sake, to that part of a conventional petri plate in which colonies are grown as the "petri plate". The cover for the petri plate we shall call the "petri plate lid". "Up" and "down" are to be understood as in the sense of the petri plate positioned to be charged with melted agar.)

The replicator of this invention comprises a petri plate lid into which is set an assembly of closely spaced, needle-like protrusions, their points directed downward; that is to say, out of the lid. A groove surrounding the needle assembly just fits the side walls of a petri plate. On the edge of the array a few of the needles are replaced with an index mark.

When the replicator is placed over, and pressed into, a master petri plate on which a master culture has been grown, the needles penetrate each and every colony on the petri plate, be the colony raised or flat, mucoid or hard. Then the replicator is removed from the master petri plate and pressed down upon the fresh agar in a new petri plate. The needles carry inoculum to the fresh plate, so that colonies grow in it in exact relationship to the colonies in the master culture. The index in the replicator indents the fresh agar to facilitate location of the several colonies. Many replications of the master culture plate can be made with a single such sampling.

DESCRIPTION OF A PREFERRED EMBODIMENT

Figure 1:
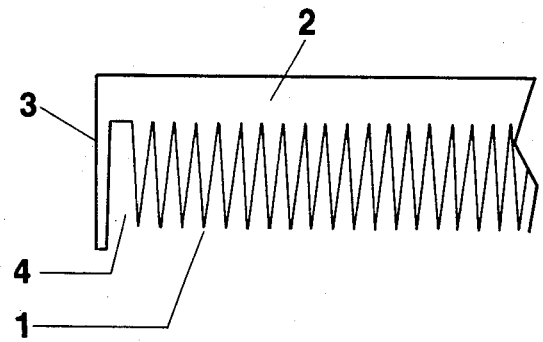
FIG. 1 is a partial cross-sectional view of the replicator.

A preferred embodiment of the replicator is illustrated in the drawings. FIG. 1 is a partial cross sction of the replicator. Externally, the replicator has the shape of a petri plate lid. Inside of the replicator, an array of pointed protrusions 1 extend downward from a solid base 2. Base 2 fits inside the side walls 3 of the replicator. The diameter of the array of protrusions 1 is about three millimeters less than the diameter of base 2, so that between the inside of the side walls 3 and the array 1 there exists a groove 4. The dimensions of groove 4 are such that, when the replicator rests on an empty petri plate, the walls of the petri plate fit into groove 4 and abut on base 2 and protrusions 1 terminate two millimeters above the bottom inside surface of the petri plate.

Side walls 3 of the replicator extend two millimeters beyond the pointed ends of the protrusions 1. Thus, the replicator can be used on a petri plate with side walls too short to reach to the bottom of groove 4, and the protrusions will still not abut on the inside bottom of the petri plate.

Figure 2:
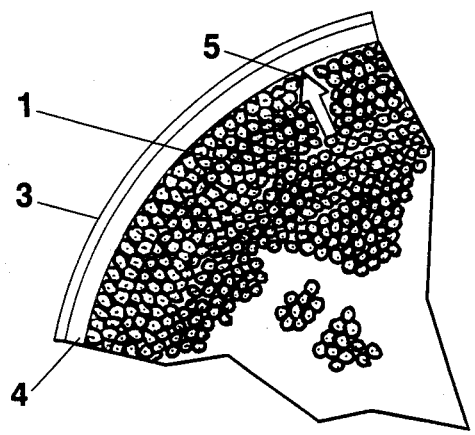
FIG. 2 is a partial worm's eye view of the replicator.

In FIG. 2, which is a worm's eye view of a quadrant of the assembled replicator, the sharp ends of protrusions 1 are shown as points. Some of the protrusions are replaced by an index mark 5.

Figure 3:
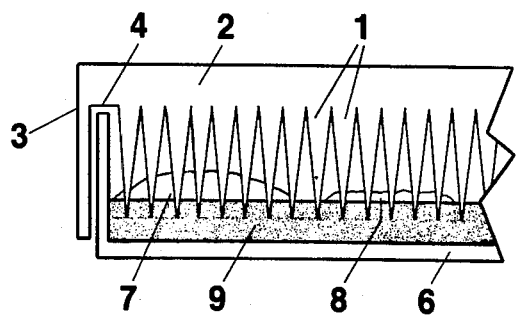
FIG. 3 is a partial cross-sectional view of the replicator, set into a petri plate on which a master culture has been grown.

In FIG. 3 the replicator is shown (in partial cross-section) in place on a petri plate 6. In the petri plate, a master culture with colonies 7 and 8 are shown growing on the surface of agar 9, which has been poured to a predetermined depth in the petri plate. Protrusions 1 puncture the surface of the agar, and in doing so, pass through the colonies. The protrusions are spaced from each other a distance such that no colony larger in diameter than a millimeter can avoid being punctured by at least one protrusion. In FIG. 3, it can be seen that the petri plate side walls, where they bottom in groove 4, limit how far the protrusions can penetrate into the the agar in the petri plate. If the petri plate side walls were too short to bottom in the groove, the replicator side walls 3 would abut the surface on which the petri plate rests. Thus the protrusions still would not contact the bottom of the petri plate, because they terminate two millimeters short of the rim of the side walls 3.

In this preferred embodiment I have found the following dimensions convenient for replicating colonies grown in a petri plate 88 millimeters in diameter with an inside wall height of 14 millimeters: The protrusions extend seven millimeters from the lower surface of base 2, which is five millimeters thick. The tips of the protrusions are 0.75 millimeters apart. I pour agar into the petri plate in which the master culture is grown, and also into the petri plates to which the master culture is to be transferred, to a depth of five millimeters. With these dimensions, the protrusions pierce the agar surface, and the colonies growing on it, to a depth of three millimeters. On the other hand a colony which has grown three millimeters above the surface of the agar will not be mashed by solid base 2. Obviously, for other size petri plates the dimensions should be changed accordingly.

The index mark 5 on the replicator makes a mark in the fresh agar during the transfer, thereby readily establishing the exact relationship of the replicated colonies to one another. With the conventional velvet pad or the RepliPlate TM, it is necessary to carefully mark the bottom of each petri plate and to make sure that the replicator is positioned in exactly the same relationship to that mark each time a new plate is inoculated.

Experiments

Experiments with needle-like protrusions made of both steel and polystyrene established that a single puncture of a colony enables at least ten growing replications of the colony. Among the microorganisms tested were colonies of actinomycetes (a particularly hard colony), Bacillus sp., a variety of fungal colonies, large raised bacterial colonies, large mucoid colonies of yeasts, flat brittle bacterial colonies, and a variety of smooth and rough bacterial colonies.

What is claimed is:
1. A cylindrical structure with peripheral side walls,
   a circumferential groove in the bottom of the structure having an outer diameter of 90 millimeters, an inner diameter of 86 millimeters, and a depth of seven millimeters,
   an array of pointed protrusions inside the groove, the points of the protrusions extending downward to within two millimeters of the bottom of the side walls, the bases of the protrusions being coplanar with the bottom of the groove, the points of the protrusions being spaced 0.75 millimeters apart, and
   a unique protrusion on the inner periphery of the groove to serve as an index mark.

* * * * *